United States Patent
Kopelman et al.

(10) Patent No.: US 7,545,372 B2
(45) Date of Patent: Jun. 9, 2009

(54) METHOD AND SYSTEM FOR IMAGING A PATIENT'S TEETH ARRANGEMENT

(75) Inventors: Avi Kopelman, Ramat Chen (IL); Eldad Taub, Reut (IL); Baruch Nissenbaum, Ramat Gan (IL)

(73) Assignee: Cadent Ltd., Or Yehuda (IL)

( * ) Notice: Subject to any disclaimer, the term of this patent is extended or adjusted under 35 U.S.C. 154(b) by 0 days.

(21) Appl. No.: 10/341,866

(22) Filed: Jan. 14, 2003

(65) Prior Publication Data

US 2003/0160784 A1    Aug. 28, 2003

Related U.S. Application Data

(60) Provisional application No. 60/348,425, filed on Jan. 14, 2002.

(51) Int. Cl.
    *G06T 15/00*    (2006.01)
(52) U.S. Cl. .................. 345/419; 345/418; 345/420; 433/213
(58) Field of Classification Search .................. 345/419, 345/420; 433/213, 214; 382/131; 700/118, 700/119, 163
    See application file for complete search history.

(56) References Cited

U.S. PATENT DOCUMENTS

| | | | |
|---|---|---|---|
| 5,237,998 A | | 8/1993 | Duret et al. .................. 128/665 |
| 5,431,562 A | * | 7/1995 | Andreiko et al. .............. 433/24 |
| 5,768,134 A | * | 6/1998 | Swaelens et al. ............ 700/121 |
| 5,823,778 A | | 10/1998 | Schmitt et al. |
| 6,243,439 B1 | * | 6/2001 | Arai et al. ...................... 378/20 |
| 6,537,066 B1 | * | 3/2003 | Azzaretto .................... 433/34 |
| 6,626,666 B2 | * | 9/2003 | Chishti et al. ................. 433/24 |
| 6,767,208 B2 | * | 7/2004 | Kaza ........................... 433/24 |
| 7,110,594 B2 | * | 9/2006 | Jones et al. .................. 382/154 |
| 2001/0002310 A1 | | 5/2001 | Chishti et al. |

(Continued)

FOREIGN PATENT DOCUMENTS

EP    0 634 150    1/1995

(Continued)

OTHER PUBLICATIONS

Chaunqi Chen, Perry Y. Li, Arthur G. Erdman, "Design and Analysis of a Four-Degree-of-Freedom Hybrid Spherical Scanning Apparatus", Univ of Minnesota, Proc of DETC'00, ASME 2000 Design Engn Tech Conf and Computers and info in Engr Conf, Baltimore, MD, Sep. 10-13, 2000.*

(Continued)

*Primary Examiner*—Ulka Chauhan
*Assistant Examiner*—Daniel F Hajnik
(74) *Attorney, Agent, or Firm*—The Nath Law Group; Jerald L. Meyer; Jiaxiao Zhang

(57) ABSTRACT

The invention provides a method and system for obtaining a three-dimensional representation of a patient's teeth arrangement. A three-dimensional physical teeth model is provided, having a surface relief corresponding to the patient's teeth arrangement. Computerized tomography (CT) is applied to the three-dimensional physical teeth model, to thereby acquire data of multiple slices of at least a portion of the teeth model. The data is analyzed to produce a virtual three-dimensional representation of the teeth model or a portion thereof.

12 Claims, 4 Drawing Sheets

U.S. PATENT DOCUMENTS

2002/0180760 A1* 12/2002 Rubbert et al. .............. 345/630
2003/0129565 A1* 7/2003 Kaza .......................... 433/213

FOREIGN PATENT DOCUMENTS

WO     WO 97/03622     2/1997
WO     WO 01/80761     11/2001

OTHER PUBLICATIONS

W. E. L. Grimson, G. J. Ettinger, S. J. White, T. Lozano-Perez, W. M. Wells, and R. Kikinis "An Automatic Registration Method for Frameless Stereotaxy, Image Guided Surgery, and Enhanced Reality Visualization" IEEE Transactions on Medical Imaging, vol. 15, No. 2, Apr. 1996.*

G. Bettega, Y. Payan, B. Mollard, A. Boyer, B. Raphaël, S. Lavallée- A simulator for maxillofacial surgery integrating 3D cephalometry and orthodontia, vol. 5 Issue 3, pp. 156-165, Published Online: Aug. 24, 2000.*

Laurendeau, Denis, et al., "A Computer-Vision Technique for the Acquisition and Processing of 3-D Profiles of Dental Imprints: An Application in Orthodontics". IEEE Transactions on Medical Imaging, vol. 10, No. 3, pp. 453-461, Sep. 1991.

* cited by examiner

METHOD AND SYSTEM FOR IMAGING A PATIENT'S TEETH ARRANGEMENT

This application claims priority to U.S. provisional application No. 60/348,425, filed Jan. 14, 2002, which is incorporated herein by reference.

FIELD OF THE INVENTION

The invention is generally in the field of dentistry and concerns a method and a system for imaging a patient's teeth arrangement.

BACKGROUND OF THE INVENTION

Obtaining dental images is of utmost importance for various dental and particularly orthodontic procedures in order to make treatment decisions, e.g. design braces, crowns or the like. These images also subsequently assist in monitoring the selected treatment.

Three-dimensional imaging and digitizing a teeth arrangement is a relatively complex procedure. Various methods have been proposed involving the direct imaging of teeth by probes forming part of an imaging system fixed to the skull. Such procedures, however, are difficult to practice.

There are also known several methods and systems for the so-called in-direct imaging of a teeth arrangement by acquiring images of a teeth model. Typically, in accordance with existing methods, a negative teeth model is obtained by utilizing a teeth impression in an appropriate matrix. An accurate positive model, typically a plaster model, is prepared from the negative model. The teeth model can be stored as such, photographed, scanned and stored digitally in a computer, etc.

Laurendeau, D., et al., *IEEE Transactions on Medical Imaging*, 10(3): 453-461, New York, USA, 1991 discloses a computer vision technique for acquiring and processing a dental image. In accordance with this technique, a standard three-dimensional teeth wax image is prepared and is optically scanned simultaneously on both sides, whereby a three-dimensional teeth image is obtained.

U.S. Pat. No. 5,237,998 discloses a three dimensional correlation of images of dental arcades, making use of an impression in the occlusive position, providing a reference in the form of three mutually spaced reference points. Three-dimensional views are taken of the impression and the points and views are also taken with the impression removed. Using the images of the reference points as a basis, the sets of views are then correlated to bring them into a single reference system.

European publication EP 634150 discloses an aid for the production of a tooth or bridge. In accordance with this technique, a model is placed on a rotary holder and during rotation is scanned by an angled scanning device.

Another technique developed by the inventors of the present invention is disclosed in WO 97/03622, which is assigned to the assignee of the present application. According to this technique, a three-dimensional representation of a teeth arrangement is obtained by providing a three-dimensional physical teeth model, removing portions of the model in a controlled, step-wise manner, and in each step, acquiring an optical image of the model or of its removed portion and digitizing each of the optical images in order to obtain a plurality of digital images. The obtained digital images are compiled to obtain a three-dimensional digital teeth representation.

GENERAL DESCRIPTION OF THE INVENTION

The present invention provides a novel method and system for creating a virtual three-dimension representation of the patient's teeth arrangement on the basis of a physical model of the teeth arrangement. In accordance with the present invention the physical model is imaged by computerized tomography (CT) to thereby create a three-dimensional image of the model and reconstruct therefrom a three-dimensional, virtual representation of the patient's teeth arrangement, which is indicative of a dental image of the patient's teeth.

The term "teeth model" will be used to denote a physical, three-dimensional representation of teeth in a solid matrix having a surface relief corresponding to the teeth arrangement of the patient. Such a model may be a "positive teeth model", comprising a teeth replica, namely, a model where each tooth is represented by a projection or bulge having contours identical in size and shape to the corresponding tooth; or a "negative teeth model", where each tooth is represented by a cavity of recess with contours identical in size, but opposite in shape to the contours of the corresponding tooth.

The term "virtual teeth model" or "virtual representation" when referring to teeth, means to denote a representation of the teeth within a computer environment, or contains a computer readable medium, that can be represented on a computer-associated display device such as a digital display or a printer.

The present invention arises out of a novel and unique concept for obtaining a three-dimensional computerized teeth representation. In accordance with the invention, a physical, three-dimensional teeth model is first prepared and is then analyzed by means of Computerized Tomography (CT), proceeding in a step-wise manner, where in each step, a slice of the model is imaged. In each step, i.e., for each slice, a two-dimensional radiation intensity profile is obtained, thus enabling the processing of a corresponding two-dimensional image representing the geometric data of the slice.

In successive steps, a plurality of sequential digital images are obtained. Then, slices-related data is analyzed by a proper combination of the sequential digital images, based, inter alia, on parameters relating to the relations between the different sequential images, a three-dimensional digital image of the teeth model is obtained.

Thus, in accordance with the invention x-ray radiation is utilized for the purpose of acquiring dental images in a manner that does not expose the patient to such radiation. Moreover, unlike prior art method and systems, in accordance with the invention. The physical model is not destroyed in the imaging process and can thus be further used, if needed.

Thus, according to one aspect of the invention, there is provided a method for obtaining a three-dimensional representation of a patient's teeth arrangement, the method comprising:

(a) providing a three-dimensional physical teeth model having a surface relief corresponding to said teeth arrangement:

(b) applying computerized tomography (CT) to said three-dimensional physical teeth model to thereby acquire data of multiple slices of at least a portion of said model;

(c) analyzing said data to produce therefrom a virtual three-dimensional representation of said at least a portion.

The invention further provides, by another of its aspects, an imaging system for carrying out the above method, the system comprising:

(a) a holder for a teeth model;

(b) a computerized tomography (CT) apparatus operable to produce geometric data of multiple slices of said model;

(c) a processor for analyzing said geometric data to thereby produce said three-dimensional representation of the teeth arrangement.

The representation may be in the form of data that is arranged for transmission or transfer to another device or system, e.g. a milling apparatus that is used to prepare a physical teeth model or a dental appliance such as a bridge or a crown that should fit into the patient's teeth. The representation may also be used to construct an image to be displayed on a computer display device, to be printed, etc. The image produced by the system may be either a complete dental image, a partial dental image, (e.g., a lingual image of a teeth section—the upper right or left sections), or may be an image of the entire cross-section of teeth or only a sectional image, etc.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DESCRIPTION OF SPECIFIC EMBODIMENTS

Figure 1:
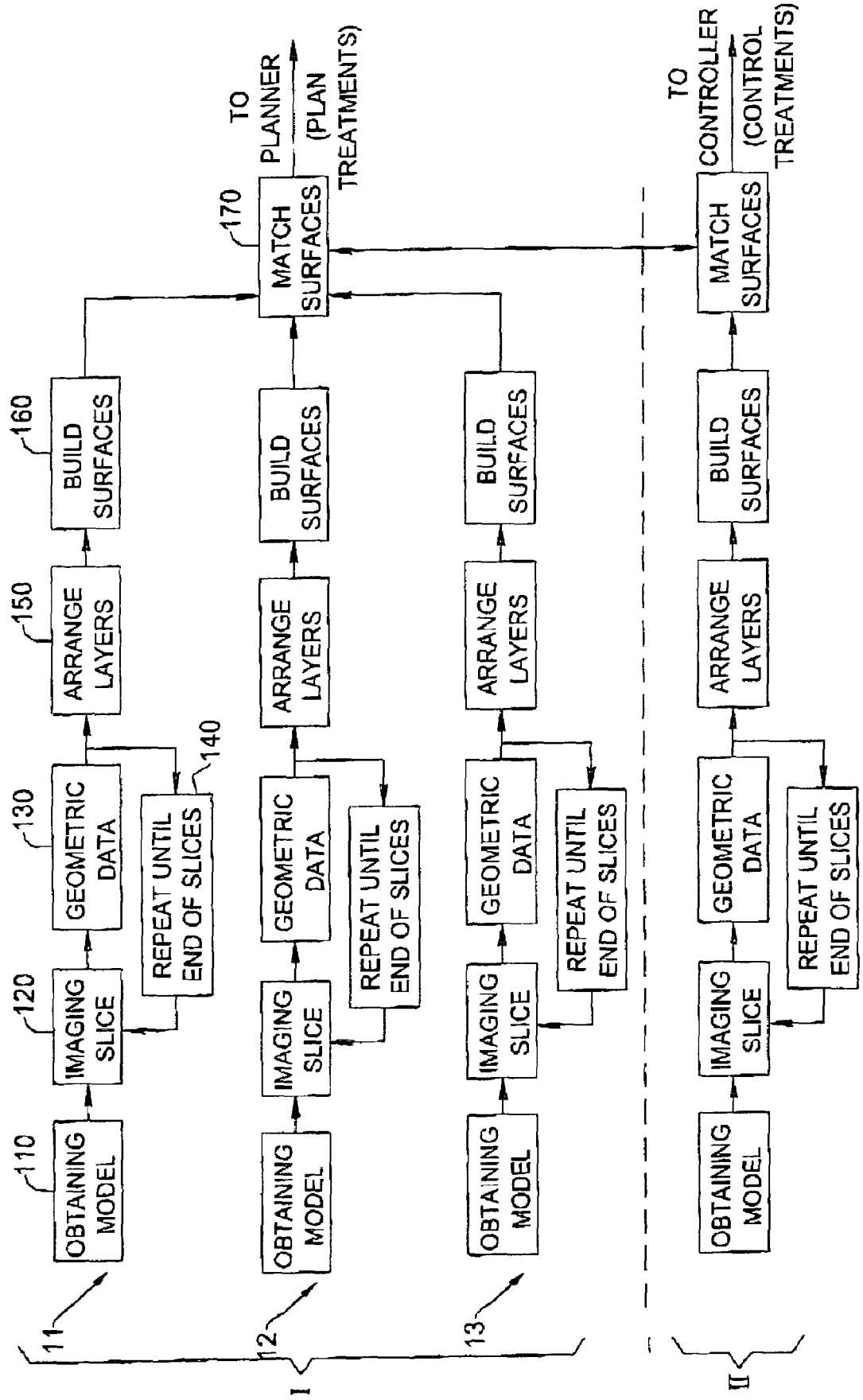
FIG. 1 is a simplified flow chart of the sequence of operations of the method in accordance with the invention.

FIG. 1 shows the sequence of operations of the method in accordance with the invention to obtain a full three-dimensional representation of a patient's teeth arrangement. This is implemented in three stages (Procedure 1): imaging an upper jaw model 11; imaging a lower jaw model 12; and imaging a model determining the relative positions of the teeth pattern in both the upper and lower jaws, 13.

To this end, a negative teeth model comprising the teeth impression is first prepared by the dentists or dental technician. A matrix in which a teeth impression in obtained will be referred to hereinbelow as "impression matrix". This negative teeth model may be used in the method as such, or may alternatively be used to prepare a positive teeth image. Preferably, a negative teeth model is used, although use of a positive teeth model is also a feasible embodiment of the invention. In the following, the invention will be described primarily in relation to the use of a negative teeth model, although it will be appreciated by person of the art that in a similar manner, mutatis mulandis, the invention may also be practiced using a positive teeth model.

Each of the negative and positive teeth models consists of a patterned structure having a surface relief corresponding to a respective portion of the patient's teeth arrangement. In the case of the negative teeth model, the structure has a pattern of a plurality of cavities, while in the case of the positive teeth model, it has a pattern of a plurality of projections or bulges. At times the cavities in a negative teeth model may be filled with a different substance than that of the model itself. The surface relief is thus the interface formed between the two substances.

Generally speaking, the teeth model is obtained by utilizing a tool which is typically a disposable impression tray. Exemplary tools suitable for use with the invention are shown in FIG. 2 and FIGS. 4a-4c. The common elements of these tools will now be described with reference to FIG. 2 only.

A typical tool 20 comprises a base 22, made of a rigid material, such as metal, plastic or the like, which holds a matrix retainer 24, having an outer wall portion 26 and an inner wall portion 28. The wall portions 26 and 28 have equal heights and define a trough-like recess 30 between them. The matrix retainer has a general C-like curvature (or configuration) which approximates that of the teeth arrangement in the jaw.

The trough-like recess 30 has a shape, allowing accommodation of all teeth in a jaw in their entirety: when the trough 30 is fitted over the teeth, the apex thereof will touch or be in close proximity to the bottom 32 of the matrix retainer, and the base of the teeth will be at about at the level of the upper surface of the wall portions 26 and 28. The inner walls 28 of the recess 30 will typically have a rough or porous surface to allow firm attachment of the impression matrix thereto.

Figure 2:
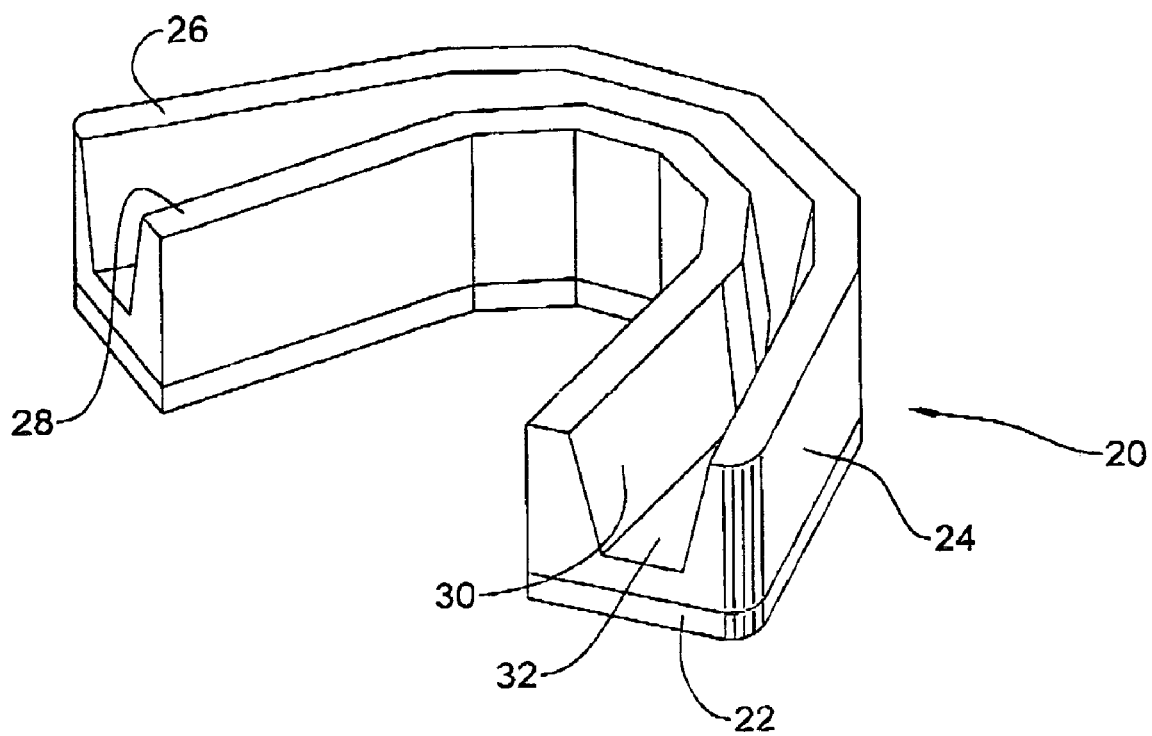
FIG. 2 is a schematic illustration of a tool for obtaining an impression of the teeth (model) of either the upper or lower jaw suitable for use with the present invention.
Figure 3:
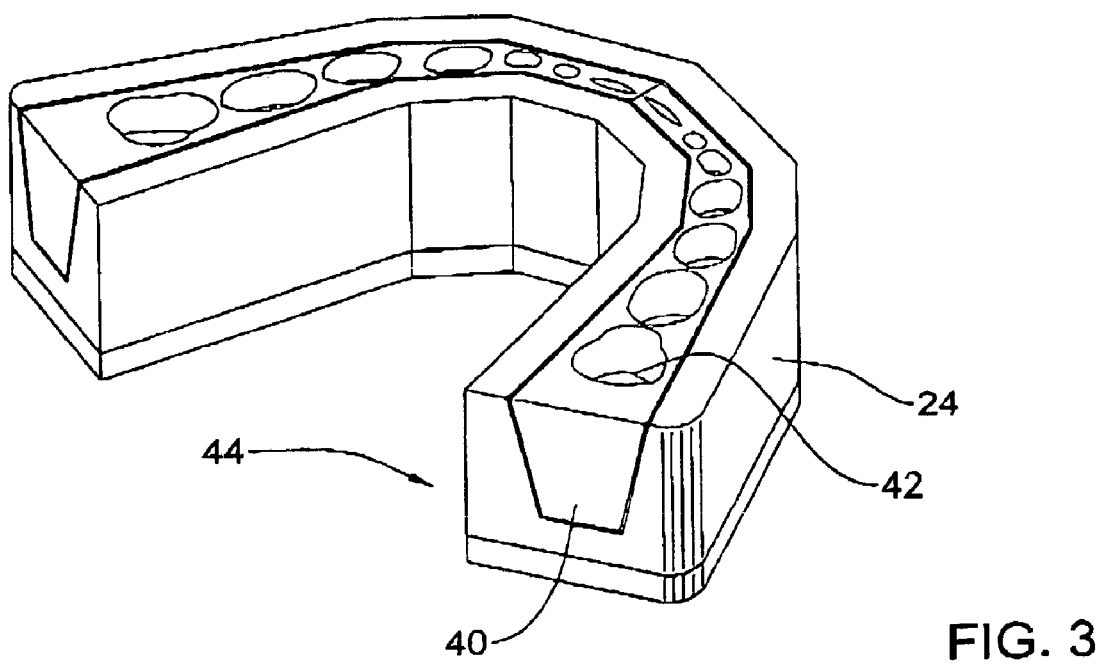
FIG. 3 is a schematic illustration of the tool of FIG. 2 containing an impression matrix with a teeth impression fixed therein.

As shown in FIG. 3, in order to obtain a negative teeth model, an impression matrix 40 is placed in the recess 30 of the tool of FIG. 2, and the tool is inserted into the patient's mouth to thereby immerse the teeth in the impression matrix. After curing the impression matrix, a plurality of cavities 42, each corresponding to certain teeth, are fixed in the matrix 40. Upon curing the impression matrix, an essentially integral block 44 is formed consisting of the matrix retainer 24 and cured impression matrix 40 with the negative teeth model that corresponds to the teeth arrangement of the patient.

Figure 4A:
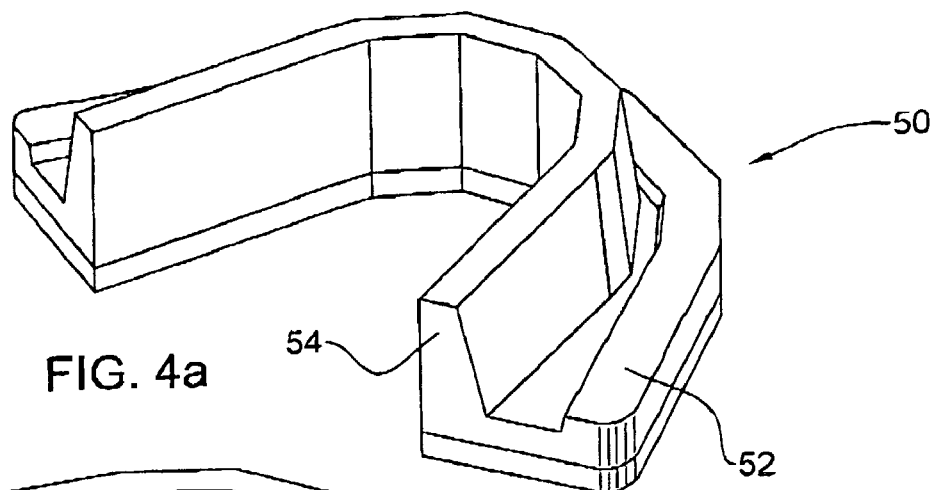
FIGS. 4a to 4c are schematic illustrations of additional examples of tools for obtaining an impression of the teeth suitable for use with the present invention.
Figure 4B:
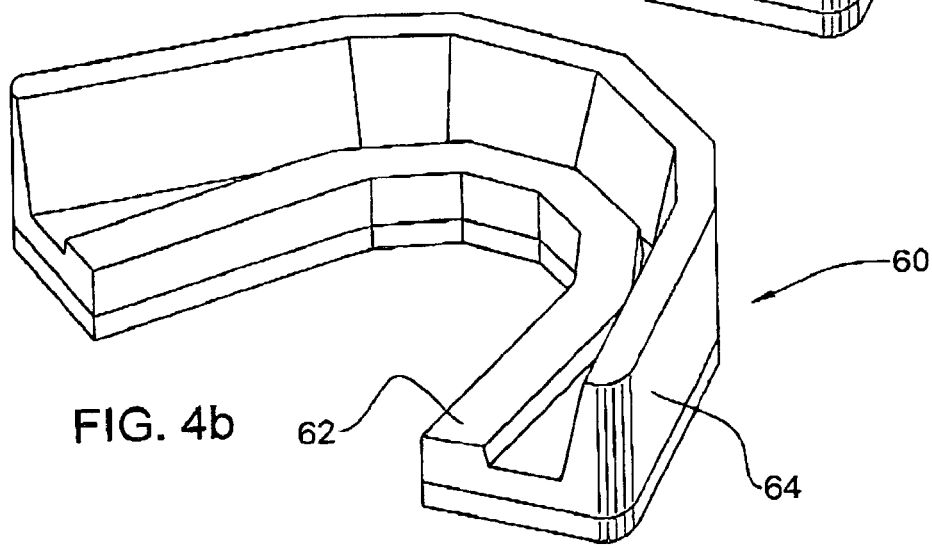
Figure 4C:
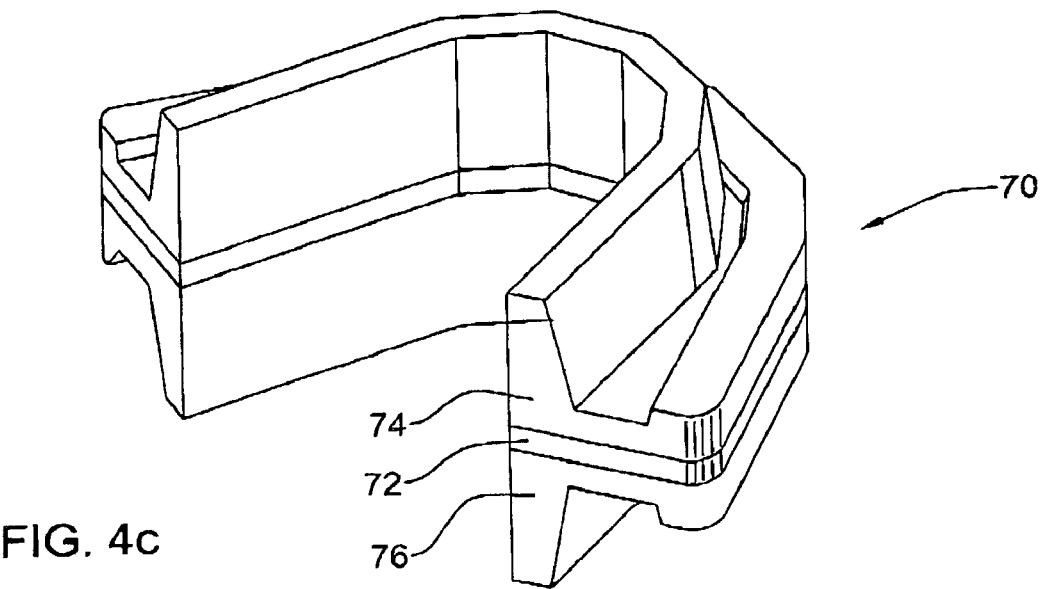

For various needs, there are also tools in which the outer wall portion and the inner wall portion of the matrix retainer do not have the same height, thus enabling to obtain only a partial dental image. FIG. 4a exemplifies a tool 50, in which an inner wall 52 is lower than an outer wall 54, thereby enabling to obtain a lingual image, or a buccal image can be obtained by using a tool 60 of FIG. 4b, in which an inner wall 62 is lower than an outer wall 64. In addition, there are tools that are double sided (e.g., having two opposite impression matrix retainers), such as a tool 70 of FIG. 4c.

It should be understood that the tools 20, 50, 60 and 70 of FIGS. 2, 4a-4c, respectively, also include such elements as a member for holding the tool, a member for securing the tool to an imaging system (CT) and the like, which are less important for the understanding of the present invention and are therefore not specifically shown. In addition, it should be noted that the invention is not limited to the exemplary tools of FIG. 2 and FIGS. 4a-4c, and any other tool suitable for obtaining a teeth model may be used with the present invention.

Turning back to FIG. 1, for imaging the upper jaw model (stage 11) and of lower jaw model (stage 12), two one-sided tools are used (one for the upper jaw and one for the lower jaw). For imaging the model of relative positions of the teeth (stage 13), a double-sided tool is needed. Each image acquisition follows essentially the same sequence of operations, and accordingly, the entire image acquisition process will be described simultaneously for acquiring all three images. Upon obtaining a negative teeth model (step 110) by using the appropriate tool with the impression matrix having the teeth impression (for example, the tool 20 with the block 44 of FIG. 3) is placed within an imaging system having a CT tools arrangement (an X-ray source and an X-ray detecting array), and is operable for acquiring a teeth impression image of a slice of the teeth model. Then, a relative displacement between this model and the CT tools arrangement is provided with reference to a specific plane of the model (step 120). This specific plane may be the plane corresponding to the teeth apex or the teeth base, i.e., having a horizontal orientation relative to the general orientation of the teeth model. The specific plane may also be vertical at one of the side, rear or front faces of the model, and furthermore, may also have an intermediate orientation between either the aforementioned horizontal or vertical orientations of the model, namely, an oblique orientation. This specific plane will be referred to hereinafter as "the model slice".

The X-ray source irradiates the relatively rotating model with a narrow X-ray beam. The X-rays passed through the model are recorded by the X-ray detecting array. Digitized information on the attenuation of the X-rays passing through the irradiated slice at various angles and at various moments of time during the rotation of the model is then used to mathematically reconstruct a two-dimensional radiation intensity profile of the slice and a corresponding two-dimensional image which represents the geometric data of the slice (step 130). Thus, each image of a single slice shows the boundaries of the surface relief of the dental model section which represents contours identical in size and shape to the corresponding slice of teeth arrangement, and the spatial information related to that slice.

In successive steps 140, a plurality of sequential digital images is obtained. The individual images, which were acquired during the repeated steps, are then digitally processed (step 150) to allow for the reconstruction of a three-dimensional teeth image (step 160). In a similar manner, three-dimensional images of the lower jaw and double-sided tray are obtained.

Then, by proper integration of the sequential digital images, based, inter alia, on parameters relating to the relation between the different sequential images, a complete dental model, i.e., a three-dimensional digital image of the patient's teeth-arrangement, is obtained (step 170).

The dental model thus obtained can then be used to plan the appropriate treatment for a patient, e.g., design braces, bridges and/or crowns, to determine the shape of implants, etc. In various orthodontic treatments, the aim is to change the position or orientation of the teeth.

Within the framework of monitoring the treatment progress, it may be sufficient to acquire a partial dental image (for example, only the lingual surfaces of the teeth). The actual image provides information on the teeth position and orientation, and, as the three-dimensional structure does not change, there actually is no need to obtain a complete teeth image. Thus, for a follow-up, Procedure II, also shown in FIG. 1, may be performed. For this purpose, a tool such as that shown in FIG. 4a may be used. The sequence of the image proceeding will be similar to that described above with respect to the imaging of a full teeth-arrangement representation.

Figure 5:
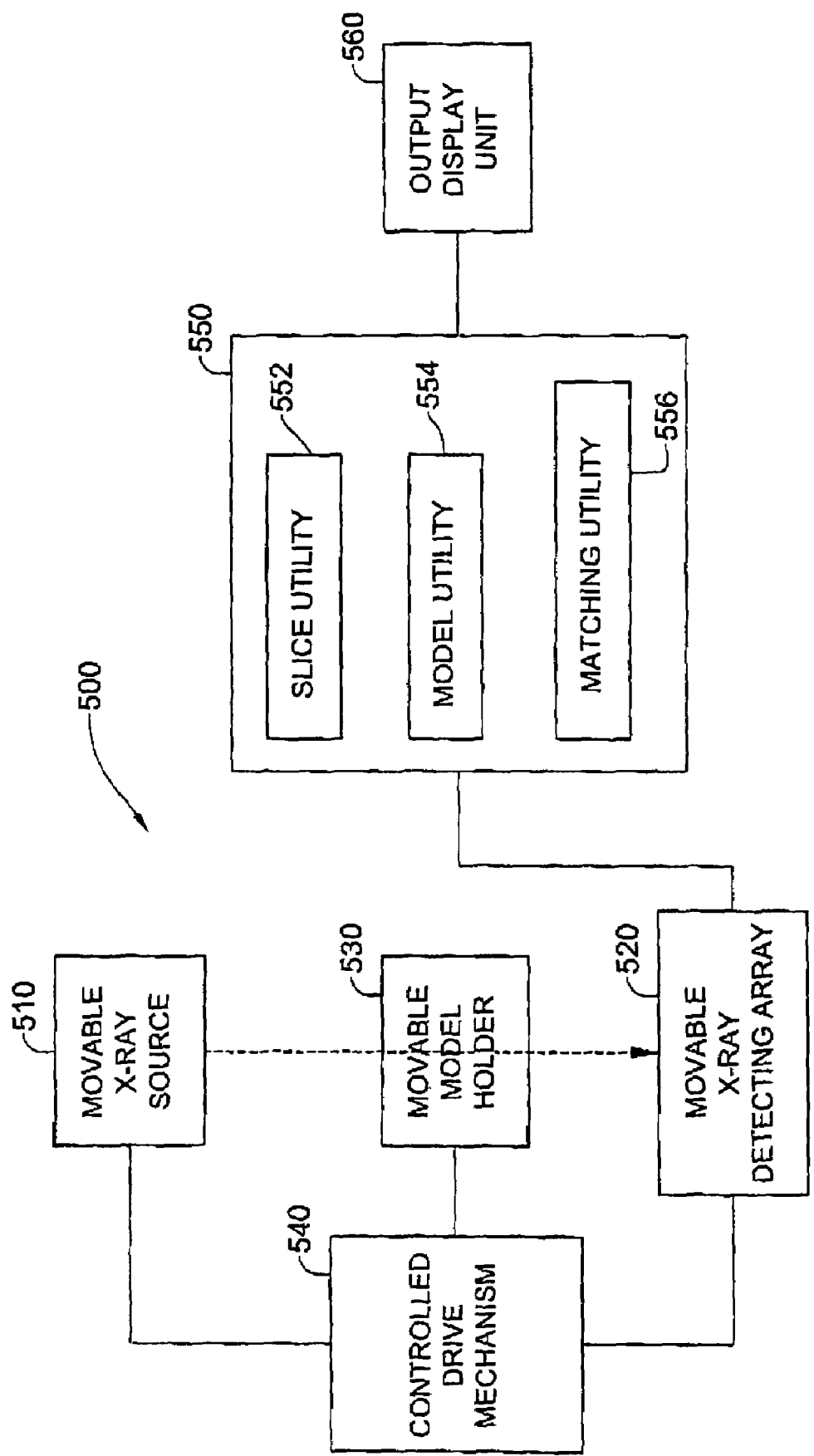
FIG. 5 is a block diagram of the main components of the system according to the invention.

Reference is now made to FIG. 5 showing a block diagram of the main components of system 500 for carrying out the invention. System 500 comprises a CT tools arrangement, including a movable X-ray source 510 capable of producing a narrow X-ray beam propagating towards a movable X-ray-detecting array 520. A movable model holder 530 is located between the source 510 and the detecting array 520, for receiving a tool with a teeth model to be imaged. Source 510, detecting array 520 and holder 530 are oriented with respect to each other, so as to ensure that the x-ray beam produced by source 510 irradiates the model in holder 530, and can be detected by detecting array 520, thus enabling the measurement of the attenuation of the X-rays passing through the irradiated model.

Source 510, detecting array 520 and holder 530 are coupled to a controlled drive mechanism 540. Detecting array 520 is also coupled to a processor 550, which comprises a slice utility 552, a model utility 554 and a matching utility 556. Output of the processor 500 is coupled to data representation unit 560, which may comprise a display.

The controlled drive mechanism 540 controls the motions of source 510, detecting array 520 and holder 530. The motions of source 510 and detecting array 520 are synchronized such that a mutual disposition is kept while both, the source, 510 and the detecting array 520 move relatively with respect to holder 530 and the model. This relative motion is formed by a first motion for imaging a single slice, and a second motion for repositioning the moving components before imaging the successive slice. The first motion allows for establishing the geometrical slice, i.e., the irradiated plane to be imaged, and the second motion allows for step-by-step imaging of successive slices.

The slice utility 552 operates to process the digitized information on the attenuation of the X-rays passing the slice, thus performing the mathematical reconstruction of the two-dimensional image of the slice. The model utility 554 successively receives the two-dimensional images of all the slices and processes them, thus allowing for the construction of a three-dimensional teeth image. The matching utility 556 is preprogrammed for the integrated processing of the acquired three-dimensional images of the upper and lower jaws and their relative position, thus enabling matching between the jaws and analysis of the complete dental model. In the above, matching utility 556 forms a part of system 500. However, matching utility 556 may be a part of an external unit which may also comprises output unit 560.

Data indicative of the complete dental model is presented through the output unit 560 Output unit 560 may be a display suitable for visual presentation of the acquired image, or a data transmitting unit for transmission of the digitized image to an external device for further analysis.

In order to obtain an accurate dental image, a CT scanning resolution in the range of 0.05-0.2 mm. is sufficient. Preferably, however, a CT tool arrangement with a resolution of 0.02 mm or less is used to thereby increase the accuracy of the image.

The invention claimed is:

1. A method for obtaining a three-dimensional representation of a patient's teeth arrangement, the method comprising:
    (a) providing a three-dimensional physical teeth model comprising an exterior model surface having a positive relief corresponding to said teeth arrangement;
    (b) applying an imaging process consisting of computerized tomography (CT) to said three-dimensional physical teeth model to thereby acquire data of multiple slices of at least a portion of said model, wherein the physical model is not destroyed in the imaging process;
    (c) analyzing said data, using CT as a primary acquired data source, to produce therefrom a plurality of sequential digital images of said at least a portion corresponding to said slices; and
    (d) producing said three-dimensional representation by integrating said plurality of sequential digital images to generate a virtual surface corresponding to said exterior model surface.

2. A method according to claim 1, wherein said model comprises a negative teeth model comprising a matrix with a plurality of cavities or recesses, each corresponding to a tooth, and wherein said cavities or recesses are filled with a different material than that of said model to form said positive model within said negative model, wherein said model surface is an outer surface of the positive model at the interface formed between the material of the negative model and that of the positive model.

3. A method according to claim 1 wherein said model is a positive teeth model, comprising a matrix with a plurality of projections or bulges, each corresponding to a tooth.

4. A method according to claim 1, wherein at least one of the model and the CT apparatus is displaced in step (b) to yield relative displacement of the two.

5. A method according to claim 4, wherein the model is being moved in order to yield said relative displacement.

6. A method according to claim 4, wherein the model and the CT apparatus are being moved in order to yield said relative displacement.

7. A method for obtaining a three-dimensional representation of a patient's teeth arrangement, the method comprising:
  (a) providing a three-dimensional physical teeth model comprising an exterior model surface having a positive relief corresponding to said teeth arrangement wherein said teeth model is a positive teeth model, comprising a matrix with a plurality of projections or bulges, each corresponding to a tooth;
  (b) applying an imaging process consisting of computerized tomography (CT) to said three-dimensional physical teeth model to thereby acquire data of multiple slices of at least a portion of said model, wherein the physical model is not destroyed in the imaging process;
  (c) analyzing said data, using CT as a primary acquired data source, to produce therefrom a plurality of sequential digital images of said at least a portion corresponding to said slices; and
  (d) producing said three-dimensional representation by integrating said plurality of sequential digital images to generate a virtual surface corresponding to said exterior model surface.

8. A method according to claim 1, further comprising the step of producing a dental appliance corresponding to a dentition surface that is based on an integration of said plurality of sequential digital images.

9. A method according to claim 1, further comprising:
  using digitized information on the attenuation of X-rays passing through an irradiated slice at various angles and at various moments of time to mathematically reconstruct a two-dimensional radiation intensity profile of the slice.

10. A method according to claim 7, further comprising:
  using digitized information on the attenuation of X-rays passing through an irradiated slice at various angles and at various moments of time to mathematically reconstruct a two-dimensional radiation intensity profile of the slice.

11. A method according to claim 1, wherein at least said step of applying an imaging process is performed at least three times: once to acquire data corresponding to an upper jaw model, once to acquire data corresponding to a lower jaw model, and once to acquire data corresponding to the relative positions of the teeth pattern in both the upper and lower jaws.

12. A method according to claim 7, wherein at least said step of applying an imaging process is performed at least three times: once to acquire data corresponding to an upper jaw model, once to acquire data corresponding to a lower jaw model, and once to acquire data corresponding to the relative positions of the teeth pattern in both the upper and lower jaws.

* * * * *